United States Patent
Gordon

(10) Patent No.: US 11,688,493 B1
(45) Date of Patent: Jun. 27, 2023

(54) MEDICATION RECONCILIATION SYSTEM AND PROCESS

(71) Applicant: Linda Ann Gordon, Longmont, CO (US)

(72) Inventor: Linda Ann Gordon, Longmont, CO (US)

( * ) Notice: Subject to any disclaimer, the term of this patent is extended or adjusted under 35 U.S.C. 154(b) by 271 days.

(21) Appl. No.: 16/165,066

(22) Filed: Oct. 19, 2018

(51) Int. Cl.
*G16H 10/60* (2018.01)
*G16H 20/10* (2018.01)

(52) U.S. Cl.
CPC ............... *G16H 10/60* (2018.01); *G16H 20/10* (2018.01)

(58) Field of Classification Search
CPC ......... G06Q 50/22; G06Q 50/24; G16H 10/60; G16H 20/10
See application file for complete search history.

(56) References Cited

U.S. PATENT DOCUMENTS

| | | | | |
|---|---|---|---|---|
| 10,503,874 | B1* | 12/2019 | Leonardo et al. | G16H 10/60 |
| 2008/0126135 | A1* | 5/2008 | Woo | G06Q 10/06 |
| | | | | 705/3 |
| 2008/0235056 | A1* | 9/2008 | Gonzalvo | G06Q 30/04 |
| | | | | 705/3 |
| 2009/0076849 | A1* | 3/2009 | Diller | G16H 10/65 |
| | | | | 705/3 |
| 2014/0172641 | A1* | 6/2014 | Sharma | G06Q 30/0623 |
| | | | | 705/26.61 |
| 2016/0048652 | A1* | 2/2016 | Spivey et al. | G16H 70/40 |
| | | | | 705/2 |
| 2019/0122140 | A1* | 4/2019 | Sen | G06N 5/022 |

FOREIGN PATENT DOCUMENTS

JP            5212960 B1 *   6/2013

OTHER PUBLICATIONS

Balaban, Dan. "Germany's Giant Health Card Project Begins to Stir." Card Technology 12.2 (2007): 26-9. ProQuest. Web. Feb. 6, 2023. (Year: 2007).*

* cited by examiner

*Primary Examiner* — Lena Najarian
(74) *Attorney, Agent, or Firm* — Plager Schack LLP; Mark H. Plager; Stephen Hallberg

(57) ABSTRACT

A medication reconciliation system that interfaces between pharmacies and healthcare providers to provide accurate patient medication history and a medication reconciliation process for providing accurate patient medication history by interfacing between pharmacies and healthcare providers are disclosed. The medication reconciliation system and process provide a level of healthcare that allows healthcare providers to accurately reconcile a patient's medication history across multiple medication supplying sources.

8 Claims, 3 Drawing Sheets

MEDICATION RECONCILIATION SYSTEM AND PROCESS

BACKGROUND

Embodiments of the invention described in this specification relate generally to recording patient prescription medication history, and more particularly, to a medication reconciliation system that interfaces between pharmacies and healthcare providers to provide accurate patient medication history and a medication reconciliation process for providing accurate patient medication history by interfacing between pharmacies and healthcare providers.

Reconciling a patient's medications is a lengthy process, sometimes riddled with errors. Also costly. Existing prescription and non-prescription medication provisioning systems lack a comprehensive way to reconcile medications corresponding to a patient. Conventionally, the existing prescription medication systems are based on a written authorization (either hand-written or delivered via computer network) from a medical authority and non-prescription medication systems have no reconciliation mechanism at all. None of the existing conventional medication systems provide reconciliation by interfaces between pharmacies and healthcare providers.

Therefore, what is needed is a way to provide reconciliation of patient medications over time by interfaces between pharmacies and healthcare providers.

BRIEF DESCRIPTION

A novel medication reconciliation system that interfaces between pharmacies and healthcare providers to provide accurate patient medication history and a novel medication reconciliation process for providing accurate patient medication history by interfacing between pharmacies and healthcare providers are disclosed. In some embodiments, the medication reconciliation system and process provide a level of healthcare that allows healthcare providers to accurately reconcile a patient's medication history across multiple medication supplying sources.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein.

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted for any of several applications.

Some embodiments of the invention include a medication reconciliation system that interfaces between pharmacies and healthcare providers to provide accurate patient medication history and a medication reconciliation process for providing accurate patient medication history by interfacing between pharmacies and healthcare providers.

In some embodiments, the medication reconciliation system and process provide a level of healthcare that allows healthcare providers to accurately reconcile a patient's medication history across multiple medication supplying sources.

As stated above, reconciling a patient's medications is a lengthy and costly process which is at times riddled with errors. Of all the conventional prescription and non-prescription medication provisioning systems in existence, none of them provide a comprehensive way to reconcile medications corresponding to a patient's medication history. Embodiments of the medication reconciliation system and process described in this specification solve such problems by providing realtime updates of a patient's medications so that accurate medication history is available to any dispensing pharmacy or prescribing medical authority, thereby ensuring that the healthcare continuum goes smoothly in the prescribing and provisioning of medication.

Embodiments of the medication reconciliation system and process described in this specification differ from and improve upon currently existing options. In particular, some embodiments differ by providing a new level of healthcare in medication arena of prescribing and provisioning medications to patients. In addition, some embodiments of the medication reconciliation system and process improve upon the currently existing options by there are no existing products that exist for medication reconciliation.

I. Medication Reconciliation System

The medication reconciliation system of the present disclosure may be comprised of the following elements. This list of possible constituent elements is intended to be exemplary only and it is not intended that this list be used to limit the medication reconciliation system of the present application to just these elements. Persons having ordinary skill in the art relevant to the present disclosure may understand there to be equivalent elements that may be substituted within the present disclosure without changing the essential function or operation of the medication reconciliation system.

Figure 1:
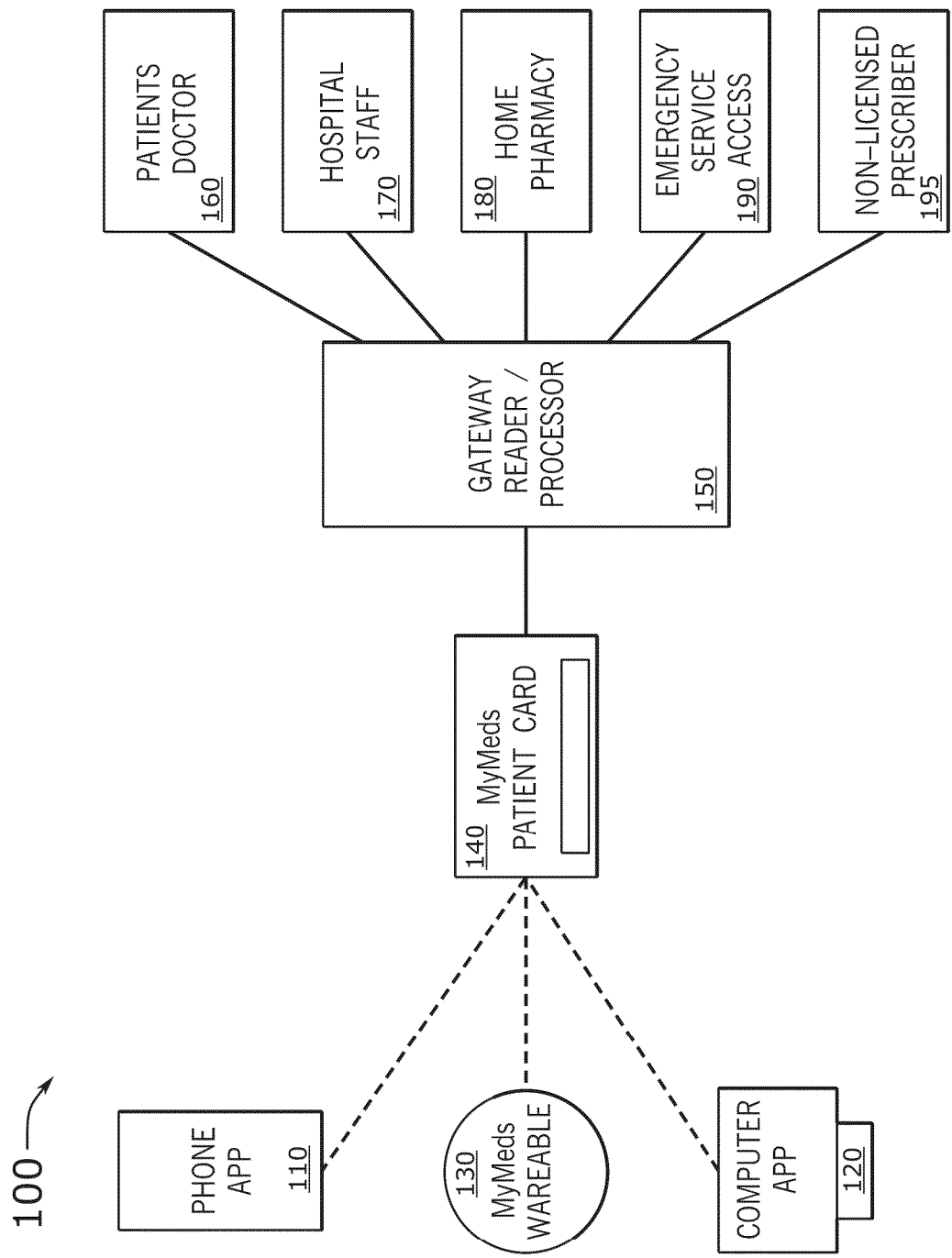
FIG. 1 conceptually illustrates a medication reconciliation system that interfaces between pharmacies and healthcare providers to provide accurate patient medication history in some embodiments.

1. patient MedRec card presented
2. Card Reader (PDQ or processing system)
3. Computer Program
4. Gateway or processor By way of example, FIG. 1 conceptually illustrates a medication reconciliation system 100 that interfaces between pharmacies and healthcare providers to provide accurate patient medication history. As shown in this figure, the medication reconciliation system 100 includes a phone app running on a digital computing device 110, a desktop software app running on a computer 120, a wearable device 130, a patient medication reconciliation card 140, and a gateway processing system 150 comprising a gateway module, a card reader, a PDQ processor. The gateway processing system 150 interfaces with software running on one or more of a patient's doctor system 160, a hospital staff system 170, a home pharmacy system 180, an emergency services access system 190, and a non-licensed prescriber system 195.

The various elements of the medication reconciliation system of the present disclosure may be related in the following exemplary fashion. It is not intended to limit the scope or nature of the relationships between the various elements and the following examples are presented as illustrative examples only. A patient specific medication reconciliation card would be used by a patient and would include identification information and typically would be about the size of a credit card and may include security elements like those of a credit card (i.e., credit card security chip, referred to as a "chipped card"). The patient would present the medication reconciliation card at a pharmacy, at a physician's office, at a hospital, or at another medical or medication provisioning facility. The patient medication reconciliation card would be swiped through the PDQ processor or information from the patient medication reconciliation card would be entered manually into a computer. A complex series of data-transfers and behind the scenes transactions and updates to patient's historical medication list would ensue to accurately record/track the patient's medication history. Furthermore, the patient's historical medication list would be refreshed and updated at the end of each visit to the pharmacy, the physician's office, the hospital, or other healthcare or medication provisioning facility. In this way, accurate, up-to-date, and current information can be given to the next healthcare provider the patient visits. The medication reconciliation system of the present disclosure is flexible enough to support medication reconciliation in emergency situations. For example, if a patient's medications were unknown when the patient entered a hospital emergency room (ER), then the patient's medication reconciliation card could be swiped at the ER to discover the patient's history of medications. Also, in some embodiments, the patient may simply use a mobile device, such as a smart phone, or a wearable device, such as a smart watch, as a form of the patient medication reconciliation card, having all relevant patient and medication history information present on the wearable device or mobile device.

The medication reconciliation system and process of the present disclosure generally works by way of the process starting when a patient medication reconciliation card is presented, either swiped through an electronic reader or entered manually into computer. Patient medication information would appear on end-user's screen, whether the end user is pharmacy, physician, or hospital. The end user could make additions or deletions to the patient's medication list to match current therapy. The list would then be closed, and the reverse process would transfer the information back to the patient card via a gateway or processor for the data transfer. Eventually, program could include use of a smartphone or wearable instead of carrying a card.

After the patient's medication reconciliation card is swiped, the gateway or processor sends information to the pharmacy, the hospital, or the provider software. Integration would be required that meets healthcare industry standards such as HIPAA and the needs of the end user. The data included on the patient's medication reconciliation card would be updated each time the patient received a new prescription or visited a hospital or physician. The gateway/processor works in reverse to update the patient's medication reconciliation card.

To make the medication reconciliation system of the present disclosure, a person with software/IT background may create a software application or computer program that implements the medication reconciliation process. Also, the medication reconciliation system may further include a secure form of a medication reconciliation card (such as a chipped card), a processor (PDQ), a gateway, an integrated computer program to be compatible with software owned by pharmacies, hospitals, and physician offices, and optional wearable components (e.g., smart watch).

To use the medication reconciliation system and process of the present disclosure, a person who prescribes, provisions, or dispenses medications to patients may solve the problem of inaccuracies in medication lists, especially when a person presents to the hospital as a new patient. For example, a person is taken to a nearby hospital in an emergency, but otherwise had no previously history with the hospital. When a new patient presents at a healthcare facility, such as a hospital, there can be significant delays in patient care, resulting in either nursing or pharmacy staff taking patient histories and needing to call the patient's usual or past pharmacy to confirm medication names and doses. However, when using the medication reconciliation system or the software application that implements the medication reconciliation process, patient medication lists would be updated in realtime, each and every time a patient is seen at a pharmacy or by a physician or at a hospital.

II. Medication Reconciliation Process

The medication reconciliation process for providing accurate patient medication history by interfacing between pharmacies and healthcare providers of the present disclosure may be comprised of the following steps. This list of possible constituent steps is intended to be exemplary only and it is not intended that this list of steps be used to limit the medication reconciliation process of the present application to just these steps. Persons having ordinary skill in the art relevant to the present disclosure may understand there to be equivalent steps, actions, functions, or operations that may be substituted within the present disclosure without changing the essential function or operation of the medication reconciliation process.

Figure 2:
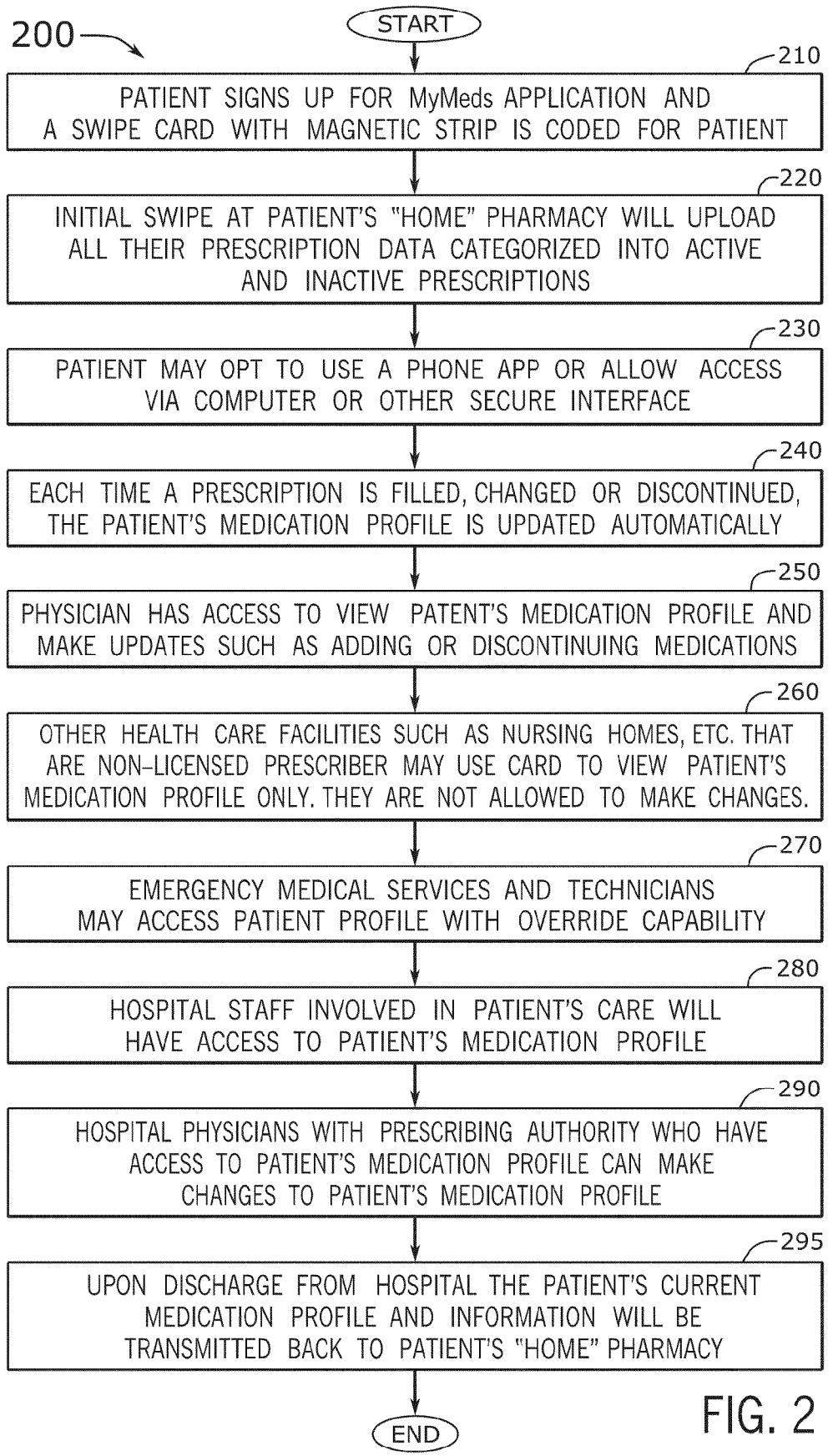
FIG. 2 conceptually illustrates a medication reconciliation process for providing accurate patient medication history by interfacing between pharmacies and healthcare providers in some embodiments.

Now turning to an example, FIG. 2 conceptually illustrates a medication reconciliation process 200 for providing accurate patient medication history by interfacing between pharmacies and healthcare providers. As shown in this figure, the medication reconciliation process 200 starts with a patient signing up (at 210) to use the medication reconciliation system. This step is for patients new to the medication reconciliation system. When the patient signs up for the medication reconciliation system, the patient will load software for interfacing with the medication reconciliation system (e.g., a "MyMeds application"). The MyMeds application will enable the patient and their healthcare providers to always have access to an up-to-date medication profile and history, thereby lessening the chance of medication errors. Patient information will be securely encrypted and accessible by PIN code, with override capability in case of emergency.

Next, the medication reconciliation process 200 proceeds to the next step during which an initial reading of the patient's medication reconciliation card is made (at 220) at the patient's present "home" pharmacy. This initial reading of the patient's medication reconciliation card at the patient's "home" pharmacy will upload all of their prescription data, categorized into active and inactive prescriptions. Inactive history will include the prior ninety days at a minimum. In some embodiments, the medication reconciliation card is a swipe card similar to a credit card, with a magnetic strip to be swiped though a processor a patient's pharmacy, physician's office, hospital or other healthcare facility. When the patient's medication reconciliation card is a swipe card, the initial reading (at 220) may be by swiping the card. Alternatively, instead of swiping the patient's medication reconciliation card, some embodiments support chipped card implementations of the patient medication reconciliation card. Chipped cards, which have a security and identity chip embedded in the card, can be used in a chipped PDQ without swiping (just inserting). Whatever manner of reading the patient's medication reconciliation card, the processors will obtain relevant information and then be linked to retail pharmacy software, utilizing block chain technology.

In some embodiments, the patient may optionally choose to use a phone app or allow access via a computer or another type of secure interface. Thus, the medication reconciliation process 200 includes the patient interface option (at 230) of phone app, computer app, other secure interface, etc., beyond merely the patient's medication reconciliation card. For instance, some of the different types of interfaces (i.e., phone app, computer app, wearable device app) are described above by reference to FIG. 1. In some embodiments, the same application will be available at retail pharmacies (same as mobile/phone app, computer application, etc.) and will integrate with pharmacy software if the patient is registered.

In some embodiments, each time a prescription is filled, changed, or discontinued, the medication reconciliation process 200 performs a step for automatically updating (at 240) the patient's medication profile. This can happen automatically when the patient's card is swiped (or patient's chipped card is inserted), upon drop-off, or after pick up of prescriptions. Similarly, automatic updating occurs when the patient logs onto the app via phone or computer.

In some embodiments, updates made by a physician, such as adding or discontinuing medications, are supported by the medication reconciliation process 200 by allowing the physician to have access to view the patient's medication profile and to catch any of the changes made by the physician (at 250) and automatically updating the patient's medication profile. For instance, the physician or personnel at the physician's office(s) may use card processors or computer software program to view the patient's medication profile and make updates such as discontinuing medications.

In some embodiments, the medication reconciliation process 200 allows other healthcare facilities to use card processors or the computer software program to view the patient's medication profile (at 260). Examples of other healthcare facilities include, without limitation, nursing homes, sub-acute care facilities, and acute care facilities. In some embodiments, the medication reconciliation process 200 limits the patient medication profile access to viewing mode only, with no changes possible for non-licensed prescribers.

In some embodiments, the medication reconciliation process 200 allows emergency medical services (EMS) and emergency medical technicians to access patient medication profile with override capability (at 270). This override capability is specifically supported in the context of EMS because the patient may not be conscious or able to speak and provide authorization for access.

Next, the medication reconciliation process 200 allows hospital staff involved in the patient's care to have access to the patient's medication profile (at 280). In particular, any staff needing access to medication information, including providers, nurses or pharmacists will be able to access the patient's medication profile and may use card processors or computer software program to access the patient's medication profile. The medication reconciliation process 200 also allows prescribing physician's or mid-level providers with prescribing authority to make changes to the patient's medication profile when or if any medication is discontinued for the patient.

In some embodiments, upon discharge from the hospital, the medication reconciliation process 200 transmits the patient's medication profile and any updated information back to the patient's "home" pharmacy. The transmittal is performed in realtime as the patient's medication profile is updated to a current status after any aforementioned updates or changes made by any one or more of the agents noted above. Then the medication reconciliation process 200 ends.

III. Electronic System

Many of the above-described features and applications are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 3:
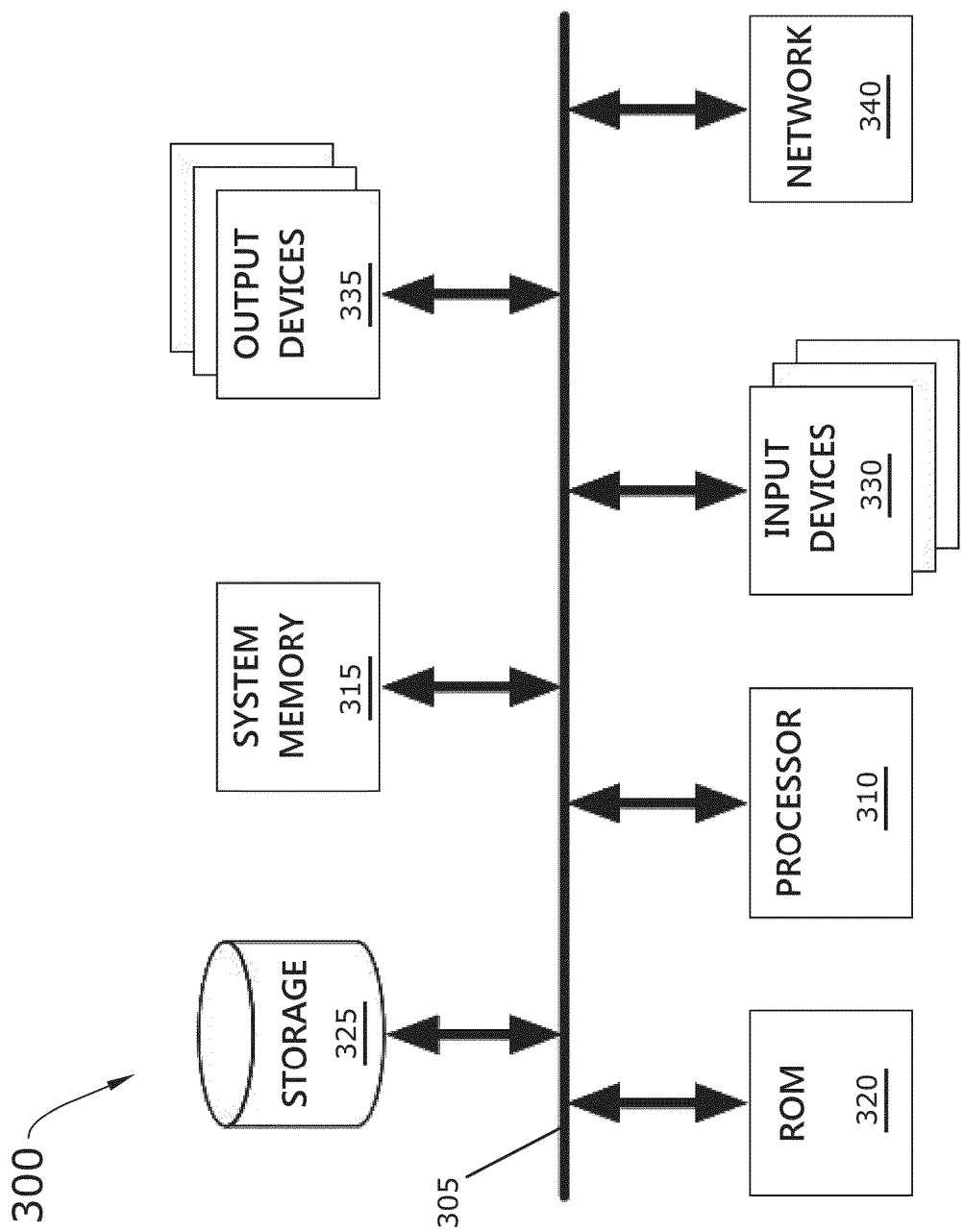
FIG. 3 conceptually illustrates an electronic system with which some embodiments of the invention are implemented.

FIG. 3 conceptually illustrates an electronic system 300 with which some embodiments of the invention are implemented. The electronic system 300 may be a computer, phone (cell phone, mobile phone, smartphone, etc.), PDA (iPod, other handheld computing device, etc.), or any other sort of electronic device or computing device. Such an electronic system includes various types of computer readable media and interfaces for various other types of computer readable media. Electronic system 300 includes a bus 305, processing unit(s) 310, a system memory 315, a read-only 320, a permanent storage device 325, input devices 330, output devices 335, and a network 340.

The bus 305 collectively represents all system, peripheral, and chipset buses that communicatively connect the numerous internal devices of the electronic system 300. For instance, the bus 305 communicatively connects the processing unit(s) 310 with the read-only 320, the system memory 315, and the permanent storage device 325.

From these various memory units, the processing unit(s) 310 retrieves instructions to execute and data to process in order to execute the processes of the invention. The processing unit(s) may be a single processor or a multi-core processor in different embodiments.

The read-only-memory (ROM) 320 stores static data and instructions that are needed by the processing unit(s) 310 and other modules of the electronic system. The permanent storage device 325, on the other hand, is a read-and-write memory device. This device is a non-volatile memory unit that stores instructions and data even when the electronic system 300 is off. Some embodiments of the invention use a mass-storage device (such as a magnetic or optical disk and its corresponding disk drive) as the permanent storage device 325.

Other embodiments use a removable storage device (such as a floppy disk or a flash drive) as the permanent storage device 325. Like the permanent storage device 325, the system memory 315 is a read-and-write memory device. However, unlike storage device 325, the system memory 315 is a volatile read-and-write memory, such as a random access memory. The system memory 315 stores some of the instructions and data that the processor needs at runtime. In some embodiments, the invention's processes are stored in the system memory 315, the permanent storage device 325, and/or the read-only 320. For example, the various memory units include instructions for processing appearance alterations of displayable characters in accordance with some embodiments. From these various memory units, the processing unit(s) 310 retrieves instructions to execute and data to process in order to execute the processes of some embodiments.

The bus 305 also connects to the input and output devices 330 and 335. The input devices enable the user to communicate information and select commands to the electronic system. The input devices 330 include alphanumeric keyboards and pointing devices (also called "cursor control devices"). The output devices 335 display images generated by the electronic system 300. The output devices 335 include printers and display devices, such as cathode ray tubes (CRT) or liquid crystal displays (LCD). Some embodiments include devices such as a touchscreen that functions as both input and output devices.

Finally, as shown in FIG. 3, bus 305 also couples electronic system 300 to a network 340 through a network adapter (not shown). In this manner, the computer can be a part of a network of computers (such as a local area network ("LAN"), a wide area network ("WAN"), or an intranet), or a network of networks (such as the Internet). Any or all components of electronic system 300 may be used in conjunction with the invention.

These functions described above can be implemented in digital electronic circuitry, in computer software, firmware or hardware. The techniques can be implemented using one or more computer program products. Programmable processors and computers can be packaged or included in mobile devices. The processes may be performed by one or more programmable processors and by one or more set of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the invention has been described with reference to numerous specific details, one of ordinary skill in the art will recognize that the invention can be embodied in other specific forms without departing from the spirit of the invention. For instance, FIG. 2 conceptually illustrates a process in which the specific operations of the process may not be performed in the exact order shown and described. Specific operations may not be performed in one continuous series of operations, and different specific operations may be performed in different embodiments. Furthermore, the process could be implemented using several sub-processes, or as part of a larger macro process. Thus, one of ordinary skill in the art would understand that the invention is not to be limited by the foregoing illustrative details, but rather is to be defined by the appended claims.

I claim:

1. A medication reconciliation system that interfaces between pharmacies and healthcare providers to provide accurate patient medication history, said medication reconciliation system comprising:
   a patient medication reconciliation card associated with and coded for a particular patient;
   a patient computing device that is operated by the particular patient to load a mobile app to securely encrypt patient information associated with the particular patient and to provide a personal identification number (PIN) code corresponding to the patient medication reconciliation card, wherein the particular patient interfaces with the mobile app for registration and sign up that allows for an initial reading of the patient medication reconciliation card at a home pharmacy of the particular patient;
   a plurality of healthcare provider systems associated with a plurality of medication supplying sources, each healthcare provider system comprising a healthcare provider computing device and a healthcare provider interface software application that runs on the healthcare provider computing device, wherein the plurality of healthcare provider systems comprises a home pharmacy healthcare provider system associated with the home pharmacy of the particular patient, said home pharmacy healthcare provider system comprising a home pharmacy healthcare provider computing device associated with the home pharmacy of the particular patient and configured to run the healthcare provider interface software application;

a gateway processing system that communicably connects the patient medication reconciliation card of the particular patient to the home pharmacy healthcare provider system, wherein the gateway processing system interfaces with the healthcare provider interface software application running on the home pharmacy healthcare provider computing device associated with the home pharmacy of the particular patient after the patient medication reconciliation card is swiped in a card reading device at the home pharmacy of the particular patient, wherein the gateway processing system (ii) transmits updated prescription data corresponding to the particular patient to the home pharmacy of the particular patient upon subsequent swipes of the patient medication reconciliation card in the card reading device at the home pharmacy;

the card reading device at the home pharmacy of the particular patient, wherein the card reading device at the home pharmacy of the particular patient (i) receives all the prescription data corresponding to the particular patient from the gateway processing system and loads all the prescription data corresponding to the particular patient received from the gateway processing system to the patient medication reconciliation card upon the initial swipe of the patient medication reconciliation card in the card reading device at the home pharmacy of the particular patient, (ii) categorizes the prescription data corresponding to the particular patient into active and inactive prescriptions for the particular patient, (iii) reads all the prescription data corresponding to the particular patient from the patient medication reconciliation card upon each subsequent swipe of the patient medication reconciliation card in the card reading device, the prescription data read upon each subsequent swipe including any prescription data changes and discontinuations associated with card reading devices at any medication supplying source in the plurality of medication supplying sources, (iv) transmits updates of active and inactive prescriptions for the particular patient to the gateway processing system when changes and discontinuations to prescriptions for the particular patient occur from any medication supplying source in the plurality of medication supplying sources, and (v) automatically updates the active and inactive prescriptions categorized on the patient medication reconciliation card, based on the changes and discontinuations to prescriptions for the particular patient, contemporaneously with transmission of the updates to the gateway processing system when the changes and discontinuations to prescriptions for the particular patient occur from any medication supplying source in the plurality of medication supplying sources.

2. The medication reconciliation system of claim 1, wherein the card reading device at the home pharmacy comprises a card processor.

3. The medication reconciliation system of claim 1, wherein the card reading device at the home pharmacy comprises a Process Data Quickly (PDQ) processor.

4. The medication reconciliation system of claim 1, wherein the patient medication reconciliation card corresponds to a medication history of the particular patient.

5. The medication reconciliation system of claim 1, wherein the healthcare provider system comprises at least one of a doctor system, a home pharmacy system, a hospital staff system, an emergency services access system, and a non-licensed prescriber system.

6. A non-transitory computer readable medium storing a medication reconciliation program which, when executed by a pharmacy computing device, interfaces between pharmacies and healthcare providers to provide accurate patient medication history based on a patient medication reconciliation card, said medication reconciliation program comprising sets of instructions for:

reading, by a Process Data Quickly (PDQ) card reading device of a gateway processing system in communication with a pharmacy computing device of a medication dispensing pharmacy, a patient medication reconciliation chipped card that includes an embedded security and identity chip, wherein the patient medication reconciliation chipped card is uniquely associated with a particular patient and is used to securely identify a medication in encrypted medication history information of the particular patient;

securely checking, in realtime and according to at least one healthcare industry standard by the gateway processing system, a plurality of medication supplying sources for external updates to the encrypted medication history information of the particular patient;

securely retrieving, by the pharmacy computing device of the medication dispensing pharmacy and according to the at least one healthcare industry standard from the gateway processing system, the identified medication in the encrypted medication history information and any external updates to the encrypted medication history information of the particular patient;

reconciling, by the pharmacy computing device of the medication dispensing pharmacy, a complete and current medication history of the particular patient based on the retrieved encrypted medication history information and any external updates to the encrypted medication history information of the particular patient;

automatically updating, according to the at least one healthcare industry standard by the pharmacy computing device of the medication dispensing pharmacy, the complete and current medication history of the particular patient based on at least one of a filling of a prescription medication, an update of a prescription medication in the complete and current medication history, and a discontinuance of a previous prescription medication in the complete and current medication history;

providing, to the gateway processing system by the pharmacy computing device of the medication dispensing pharmacy and according to the at least one healthcare industry standard, the automatically updated complete and current medication history of the particular patient;

updating, by the gateway processing system according to the at least one healthcare industry standard, an encrypted medication profile of the particular patient with all prescription data of the particular patient in the complete and current medication history of the particular patient by way of the patient medication reconciliation chipped card to make the complete and current medication history of the particular patient securely encrypted when stored in a blockchain accessible to the gateway processing system and associated with a secure personal identification number (PIN) encoded on the chipped card and available to at least a home pharmacy of the particular patient among the plurality of medication supplying sources;

receiving, from a second patient operating a second device comprising one of a mobile device running a mobile app operated by the second patient and a conventional computing device running a software program operated by the second patient, patient information associated with the second patient signing up with the second device to use a medication reconciliation system in connection with a second patient medication reconciliation magnetic stripe card, wherein the patient information associated with the second patient comprises encrypted medication information about the second patient, wherein the encrypted medication information about the second patient is encrypted according to Health Insurance Portability and Accountability Act (HIPAA) healthcare industry standards for medical record data privacy, and secured by a second patient-provided PIN code for decoded access to the encrypted medication information about the second patient, wherein the encrypted medication information about the second patient comprises prescription data of the second patient, wherein the medication reconciliation program further comprises a set of instructions for performing an initial reading of the second patient medication reconciliation magnetic stripe card by a card reading device of the gateway processing system in communication with the pharmacy computing device of the medication dispensing pharmacy, wherein the initial reading of the second patient medication reconciliation magnetic stripe card by the card reading device of the gateway processing system in communication with the pharmacy computing device of the medication dispensing pharmacy uploads the prescription data of the encrypted medication information about the second patient to a screen of the pharmacy computing device for viewing by a pharmacist, wherein the medication reconciliation program further comprises sets of instructions for:

automatically (i) updating, by the gateway processing system according to the at least one healthcare industry standard, the prescription data of the encrypted medication information about the second patient to reflect particular discontinued prescription data when a particular prescription is discontinued and to make an up-to-date medication profile and history of the second patient to securely encrypt and (ii) uploading all medication data of the second patient, including the updated prescription data, to the second patient medication reconciliation magnetic stripe card; and categorizing the medication data on the second patient medication reconciliation magnetic stripe card into an active prescription category and an inactive prescription category, wherein the particular discontinued prescription data reflected in the updated prescription data is categorized in the inactive prescription category, wherein the medication data comprises the automatically updated and uploaded medication data, including the updated prescription data, on the second patient medication reconciliation magnetic stripe card categorized for the second patient and all medication data in the medical profile of the particular patient on the patient medication reconciliation chipped card, said medication data categorized into active and inactive prescriptions on the respective patient medication reconciliation card.

7. The non-transitory computer readable medium of claim 6, wherein the set of instructions for automatically updating the complete and current medication history comprises sets of instructions for responding to at least one of (i) a physician of the particular patient updating at least one of the prescribed medications in the active prescription category for the particular patient via a doctor computing device associated with the physician, (ii) an emergency medical services personnel of the particular patient overriding and updating at least one of the prescribed medications in the active prescription category and the inactive prescription category for the particular patient via an emergency medical services (EMS) computing device, and (iii) the physician of the patient discontinuing at least one previous prescription medication in the active prescription category for the particular patient via the doctor computing device, wherein the discontinued previous prescription medication is re-categorized into the inactive prescription category for the particular patient on the patient medication reconciliation chipped card.

8. The non-transitory computer readable medium of claim 6, wherein the set of instructions for automatically updating the complete and current medication history comprises sets of instructions for:

detecting when a prescription medication is one of filled, changed, and discontinued; and automatically updating the complete and current medication history of the particular patient upon one of reading the patient medication reconciliation chipped card uniquely associated with the particular patient, receiving a drop-off of a prescription, and receiving a pick-up of a prescription.

* * * * *